United States Patent
Wang et al.

(10) Patent No.: US 8,423,121 B2
(45) Date of Patent: Apr. 16, 2013

(54) METHOD AND SYSTEM FOR GUIDEWIRE TRACKING IN FLUOROSCOPIC IMAGE SEQUENCES

(75) Inventors: Peng Wang, Princeton, NJ (US); Ying Zhu, Monmouth Junction, NJ (US); Wei Zhang, Plainsboro, NJ (US); Terrence Chen, Princeton, NJ (US); Peter Durlak, Erlangen (DE); Ulrich Bill, Effeltrich (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 650 days.

(21) Appl. No.: 12/538,456

(22) Filed: Aug. 10, 2009

(65) Prior Publication Data
US 2010/0121181 A1    May 13, 2010

Related U.S. Application Data

(60) Provisional application No. 61/087,760, filed on Aug. 11, 2008.

(51) Int. Cl.
*A61B 5/05* (2006.01)

(52) U.S. Cl.
USPC .............. 600/424; 600/425; 382/102

(58) Field of Classification Search ........... 600/317, 600/321, 329, 411, 427, 434, 435, 438; 606/27, 606/28, 41, 45; 382/128, 130, 154, 160
See application file for complete search history.

(56) References Cited

U.S. PATENT DOCUMENTS

| | | | |
|---|---|---|---|
| 6,577,889 B2 * | 6/2003 | Ichihashi | 600/425 |
| 6,778,689 B1 | 8/2004 | Aksit et al. | |
| 2004/0073120 A1 * | 4/2004 | Motz et al. | 600/478 |
| 2006/0058643 A1 * | 3/2006 | Florent et al. | 600/423 |
| 2006/0184016 A1 * | 8/2006 | Glossop | 600/434 |
| 2007/0189580 A1 * | 8/2007 | Slabaugh et al. | 382/103 |
| 2007/0270692 A1 * | 11/2007 | Barbu et al. | 600/431 |
| 2008/0247621 A1 | 10/2008 | Zarkh et al. | |

OTHER PUBLICATIONS

Barbu, A. et al., "Hierarchical Learning of Curves Application to Guidewire Localization in Fluoroscopy", in (CVPR). 2007.
Mazouer, P. et al., "User-Constrained Guidewire Localization in Fluoroscopy", in (Medical Imaging: Image Processing), Proc. SPIE, 2009.

* cited by examiner

*Primary Examiner* — James Kish
*Assistant Examiner* — Michael N Fisher (57) ABSTRACT

A method and system for tracking a guidewire in a fluoroscopic image sequence is disclosed. In order to track a guidewire in a fluoroscopic image sequence, guidewire segments are detected in each frame of the fluoroscopic image sequence. The guidewire in each frame of the fluoroscopic image sequence is then detected by rigidly tracking the guidewire from a previous frame of the fluoroscopic image sequence based on the detected guidewire segments in the current frame. The guidewire is then non-rigidly deformed in each frame based on the guidewire position in the previous frame.

30 Claims, 5 Drawing Sheets

METHOD AND SYSTEM FOR GUIDEWIRE TRACKING IN FLUOROSCOPIC IMAGE SEQUENCES

This application claims the benefit of U.S. Provisional Application No. 61/087,760, filed Aug. 11, 2008, the disclosure of which is herein incorporated by reference.

BACKGROUND OF THE INVENTION

The present invention relates to x-ray imaging, and more particularly, to guidewire tracking in 2D fluoroscopic image sequences.

Coronary intervention, or coronary angioplasty, is a common medical procedure for treating heart disease. During such a coronary intervention procedure, a guidewire is inserted into a patient's blood vessels and guided to a stenosis or blockage in the coronary arteries. In image guided cardiac interventions, automatic guidewire tracking has important applications. Since a low dose of radiation and contrast materials is desirable during interventions, fluoroscopic images captured during interventions typically have low image quality. This leads to low visibility of vessels, catheters, and guidewires during intervention procedures. Automatic guidewire tracking can help to improve the visibility of a guidewire, and assist clinicians in obtaining high precision in image-guided interventions.

Figure 1:
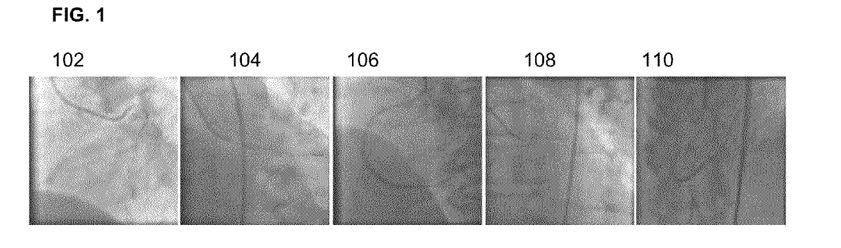
FIG. 1 illustrates guidewires in exemplary fluoroscopic images.

Guidewire tracking in fluoroscopic image sequences is challenging. Guidewires are thin and typically have low visibility in fluoroscopic images, which typically have poor image quality due to the low dose of radiation used in interventional imaging. FIG. 1 illustrates guidewires in exemplary fluoroscopic images 102, 104, 106, and 108. Sometimes segments of guidewires are barley visible in noisy images. Such weak and thin guidewire structures in noisy images make robust tracking difficult. Guidewires also exhibit large variations in their appearances, shapes, and motions. The shape deformation of a guidewire is mainly dues to a patient's breathing and cardiac motions in 3D, but such 3D motions are complicated when being projected onto a 2D image space. Furthermore, there may exist other wire-like structures, such as guiding catheters and ribs, in fluoroscopic images.

Since a guidewire is thin, tracking methods that use regional features, such as holistic intensity, textures, and color histogram, cannot track a guidewire well. Active contour and level set based methods rely heavily on intensity edges, so they are easily attracted to image noise and other wire-like structures in fluoroscopic images. Furthermore, active contour and level set based methods can only track closed contour, while the guidewire is an open curve. Considering the noise level in typical fluoroscopic images, existing methods cannot deliver desired speed, accuracy, and robustness for coronary interventions. Accordingly, a guidewire tracking method that is fast, robust, and accurate is desirable.

BRIEF SUMMARY OF THE INVENTION

The present invention provides a method and system for guidewire tracking in fluoroscopic image sequences. Embodiments of the present invention provide a hierarchical framework to continuously and robustly track a guidewire for image-guided interventions. The hierarchical guidewire tracking framework utilizes three main stages of learning based guidewire segment detection, rigid guidewire tracking across successive frames of a fluoroscopic image sequence, and non-rigid guidewire deformation. Each of the stages handles deformation of a guidewire at a specific level, and their combination provides robust tracking results.

In one embodiment of the present invention, guidewire segments are detected in a plurality of frames of the fluoroscopic image sequence. The guidewire in a current frame of the fluoroscopic image sequence is then detected by rigidly tracking the guidewire from a previous frame of the fluoroscopic image sequence based on the guidewire position in the previous frame and the detected guidewire segments in the current frame. The detected guidewire in the current frame is then non-rigidly deformed based on the guidewire position in the previous frame.

These and other advantages of the invention will be apparent to those of ordinary skill in the art by reference to the following detailed description and the accompanying drawings.

DETAILED DESCRIPTION

The present invention relates to a method and system for guidewire tracking in fluoroscopic image sequences. Embodiments of the present invention are described herein to give a visual understanding of the guidewire tracking method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a hierarchical method of tracking a guidewire in a fluoroscopic image sequence. This method can track large and non-rigid guidewire motions in fluoroscopic image sequences. The guidewire tracking method includes three stages of learning-based guidewire segment detection, rigid guidewire tracking, and non-rigid guidewire deformation. Each stage addresses the guidewire tracking problem at a specific level, and their combination provides robust guidewire tracking results.

At each frame in a fluoroscopic image sequence, learning based guidewire segment detection is used to automatically detect small segments of a guidewire. The detected segments are used as primitive features for guidewire tracking. After the guidewire segments have been detected, a hierarchical tracking scheme is applied to robustly track the guidewire based on the detected segments. Since the guidewires exhibit large variations in shape and motion, especially due to projections from 3D to 2D, the method, according to an embodiment of the present invention, does not assume that the 3D projection information is available and no guidewire motion is imposed that depends on such 3D information. Instead, according to an embodiment of the present invention, the method attempts to handle guidewire motion that could be captured from arbitrary directions. For this purpose, the method decomposes the guidewire motion into two major steps: rigid and non-rigid motion, as the guidewire motion caused by respiratory motion can be approximated as rigid motion in 2D and the guidewire motion caused by cardiac motion is non-rigid.

Figure 2:
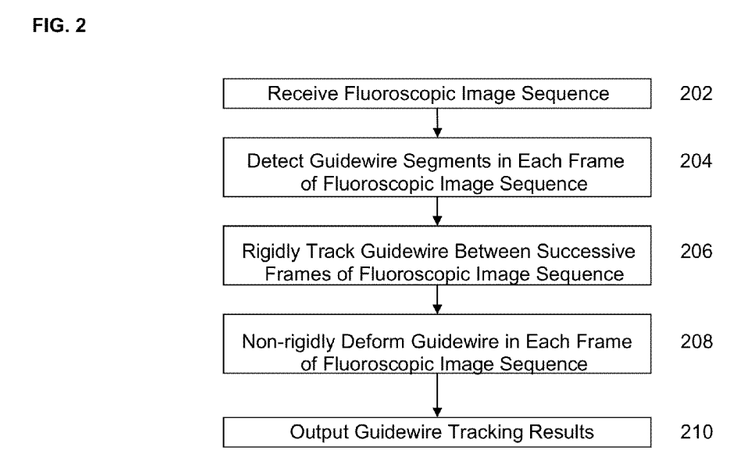
FIG. 2 illustrates a method of tracking a guidewire in a fluoroscopic image sequence according to an embodiment of the present invention.

FIG. 2 illustrates a method for tracking a guidewire in a fluoroscopic image sequence according to an embodiment of the present invention. The method of FIG. 2, transforms image data representing human anatomy, such as blood vessels and surrounding tissue, in order to track a guidewire in the vessels by generating images showing the guidewire in the frames of an image sequence. As illustrated in FIG. 2, at step 202, a fluoroscopic image sequence is received. The fluoroscopic image sequence can be a sequence of low dose 2D fluoroscopic (x-ray) images taken over a period of time. Each image in the fluoroscopic image sequence is referred to herein as a "frame". The fluoroscopic image sequence can be received directly from an x-ray imaging device that captured the images. For example, the fluoroscopic image sequence can be received from an x-ray imaging device as the fluoroscopic images are captured by the x-ray imaging device. It is also possible that the fluoroscopic image sequence is received by loading a previously generated fluoroscopic image sequence from a computer readable medium, or memory or storage of a computer system.

Figure 3:
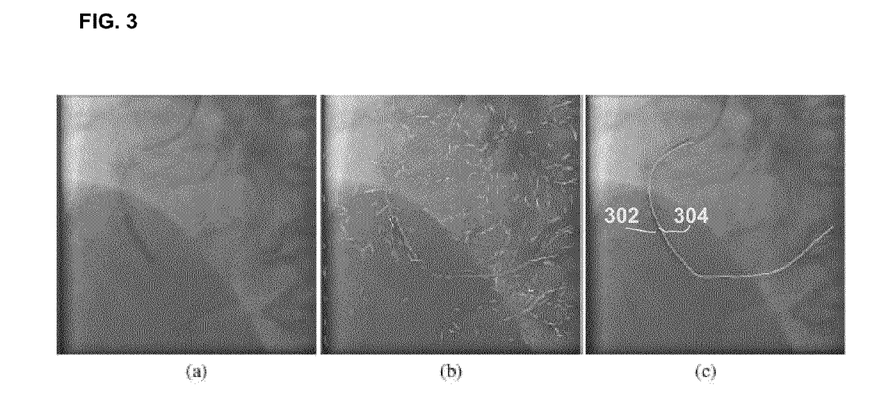
FIG. 3 illustrates guidewire tracking results resulting from various steps of the method of FIG. 2 in an exemplary frame of a fluoroscopic image sequence.

FIG. 3 illustrates guidewire tracking results resulting from various steps of the method of FIG. 2 in an exemplary frame of a fluoroscopic image. Image (a) of FIG. 3 shows an exemplary frame of a received fluoroscopic image sequence.

Returning to FIG. 2, at step 204, guidewire segments are detected in each frame of the fluoroscopic image sequence. According to an advantageous implementation, learning based guidewire segment detection is used to independently detect segments of the guidewire in each frame of the fluoroscopic image sequence. The detected guidewire segments in the frames of the fluoroscopic image sequence are used as primitives for guidewire tracking in steps 206 and 208.

It is critical to properly represent a guidewire for robust tracking. The shape of a guidewire can be represented as a spline curve, however, the appearance of the guidewire is difficult to distinguish in fluoroscopic images due to background noises and weak visibility of the guidewire. Traditional edge and ridge detectors detect line segments based on derivatives of image intensity, but such detectors may miss some thin guidewires and detect many false segments. According to an embodiment of the present invention, a learning based guidewire segment detection method is used. This learning based guidewire segment detection method can identify weak guidewire segments and modestly suppress false detections.

The learning based guidewire detection method uses a probabilistic boosting tree (PBT) to train a guidewire segment detector based on annotated training data. PBT is a supervised method extended from the well-known AdaBoost algorithm, which combines weak classifiers into a strong classifier. PBT further extends AdaBoost into a tree structure and is able to model complex distributions of objects, which is desirable in handling different types of guidewires in fluoroscopy. According to an advantageous implementation, Haar features are extracted from images as the features used in the PBT classifier. Haar features measure image differences of many configurations and are fast to compute. In order to train the guidewire segment detector, numerous guidewires are collected (e.g., annotated) from fluoroscopic images. Segments of the guidewires are cropped as positive training samples and image patches outside the guidewires are used as negative training samples. The training samples are then used to train the PBT based guidewire segment detector offline.

During guidewire segment detection of an input image, such as a frame of the received fluoroscopic image sequence, the trained guidewire segment detector can identify online if a patch of the image belongs to a guidewire or the background. The output of the PBT-based guidewire segment detector, denoted as P(x) given an image patch at the position x, is a combination of outputs from a collection of learned weak classifiers $H_k(x)$ with associated weights $\alpha_k$. The numeric output can be further interpreted as probabilistic measurements of guidewire segments, as expressed in Equation (1):

$$f(x) = \sum_k \alpha_k H_k(x) \qquad (1)$$

$$P(x) \propto \frac{e^{f(x)}}{e^{-f(x)} + e^{f(x)}}.$$

An image patch at the position x can be classified as a guidewire segment if P(x) is greater than a threshold (e.g., P(x)>0.5), and classified as background if P(x) is not greater than the threshold. Further, in order to detect guidewire segments at different orientations, each frame can be rotates at a number (e.g., 30) of discretized orientations for detection. As illustrated in FIG. 3, image (b) shows guide wire segments detected by the trained guidewire detector in the frame shown in image (a).

Returning to FIG. 2, at step 206, the guidewire is rigidly tracked across successive frames of the fluoroscopic image sequence based on the detected guidewire segments. This rigid tracking searches for the rigid motion of a guidewire between two successive frames using the detected guidewire segments as primitive guidewire features. For a current frame, the guidewire position and shape is detected by rigidly tracking the guidewire from a previous frame based on the guidewire position and shape n in the previous frame and the detected guidewire segments in the current frame. At the first frame in the fluoroscopic image sequence, the guidewire can be either automatically detected based on the by detected guidewire segments, or can be initialized by an interactive guidewire detection method. For example, an automated guidewire detecting method is described in Barbu et al., "Hierarchical Learning of Curves Application to Guidewire Localization in Fluoroscopy," CVPR (2007), which is incorporated herein by reference, and an interactive guidewire detection method is described in Mazouer et al., "User-Constrained Guidewire Localization in Fluoroscopy," *Medical Imaging: Image Processing*, Proc. SPIE (2009).

In the rigid guidewire tracking, the detected segments on a guidewire in a previous frame are used as template, denoted as T. The line segments detected at the current frame are used as observed primitive features, denoted as I. Given the template T and the observation I, the rigid tracking determines the best matching between T and I under a rigid motion model. This rigid tracking can be formalized as the maximization of a matching score, which is defines as $E_m$ in Equation (2):

$$E_m(\vec{u}) \left( \sum_i \sum_j P(I(j)) \exp\left\{ -\frac{|T(i;\vec{u}) - I(j)|^2}{2\sigma^2} \right\} \right). \quad (2)$$

In Equation (2), the template and observation are represented as their spatial position, and $\vec{u}$ is the parameter of a rigid transformation. $T(i;\vec{u})$ denotes the i-th segment of the guidewire template under the rigid transformation $\vec{u}$. $I(j)$ denotes the j-th detected guidewire segment at the current frame. $P(I(j))$ is the probabilistic output from the PBT based guidewire segment detector, indicating the confidence of the j-th detected guidewire segment. The Euclidean distance $|T(i; \vec{u}) - I(j)|$ is used to measure the distance between the template and the guidewire primitive features under the rigid motion parameter $\vec{u}$, and $\sigma$ is the kernel bandwidth. By varying the kernel bandwidth $\sigma$, the matching score can be calculated at different resolutions. Using a greater $\sigma$ measures the similarity between guidewire templates and the detected guidewire segments at a finer resolution. Accordingly, the rigid tracking finds the best rigid transformation $\vec{t}$ that maximizes the matching score $E_m$, i.e., $$\vec{t} = \arg\min_{\vec{u}} E_m(\vec{u}).$$

Figure 4:
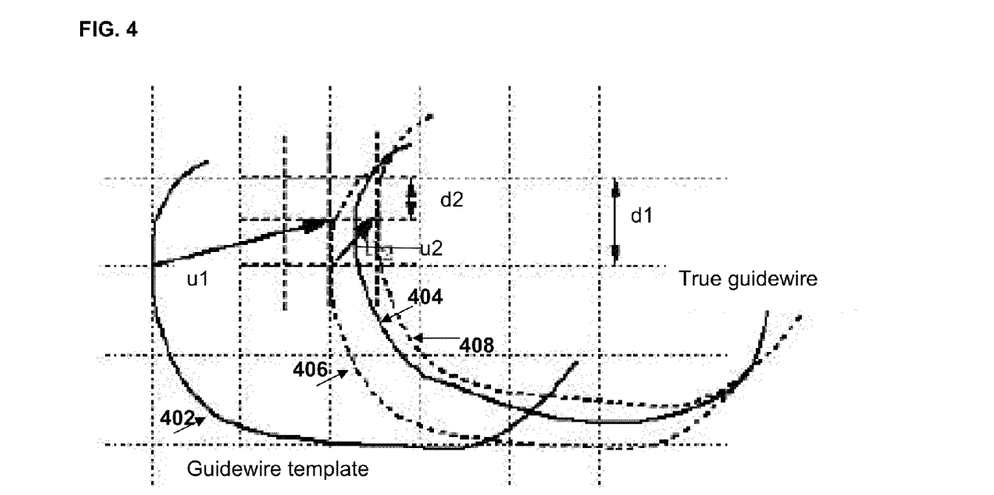
FIG. 4 illustrates multi-resolution rigid tracking with variable kernel bandwidths.

Calculating the matching score in Equation (2) can be costly when there are many detected segments in an image. For computational efficiency, it is possible to assume that a rigid motion is mainly caused by the translation, and the energy minimization of Equation (2) can be efficiently implemented by using variable kernel bandwidths in the maximization of Equation (2). FIG. 4 illustrates multi-resolution rigid tracking with variable kernel bandwidths. As illustrated in FIG. 4 guidewire template 402 is the guidewire detected at a previous frame, and true guidewire 404 is the true location of the guidewire in the current frame. The rigid tracking is performed at multiple resolutions with decreased search intervals $\{d_1 > d_2 > \ldots > d_T\}$ at an image grid. During the multi-resolution tracking, the corresponding bandwidth in Equation (2) varies accordingly, denoted as $\sigma_i$. At lower resolutions, larger kernel bandwidths are used to avoid missing guidewire tracking caused by larger sampling intervals, and at higher resolutions, smaller kernel bandwidths are used to obtain finer tracking results. According to an advantageous implementation, we set $\sigma_i = d_i$, $i=1, \ldots, T$, to adapt the multi-resolution rigid tracking. As shown in FIG. 4, at search interval $d_1$ the rigid transformation $u_1$ is selected to maximize $E_m$, resulting in guidewire tracking result 406. At search interval $d_2$, the rigid transformation $u_2$ is selected to maximize $E_m$, resulting in guidewire tracking result 408.

According to an embodiment of the present invention, the rigid tracking can be performed at both global and local scales. At the global scale, the whole guidewire is tracked between successive frames, while at the local scale, the whole guidewire is divided into several local segments, and each segment is rigidly tracked between successive frames. In this embodiment, the rigid guidewire tracking can first globally track the whole guidewire, and then adjust the tracking results by rigidly tracking each local segment of the guidewire. The rigid tracking at the global and local scales both follow the same formalization expressed in Equation (2). By using this two-stage rigid tracking, the guidewire is roughly tracked to each frame in the fluoroscopic image sequence. Image (c) of FIG. 3 shows a guidewire tracking result 302 resulting from the rigid guidewire tracking.

Returning to FIG. 2, at step 208, the guidewire is non-rigidly deformed in each frame of the fluoroscopic image sequence in order to further track the guidewire. In particular, in a current frame the guidewire detected by rigid tracking is non-rigidly deformed based on the rigidly tracked guidewire position and shape and the detected guidewire segments in the current frame.

Starting from the guidewire aligned by the rigid tracking, the non-rigid tracking further refines the guidewire shape to recover the non-rigid motions of a guidewire. In the non-rigid tracking, a matching score is also maximized between a guidewire template and the observed guidewire primitive features. However, different from the rigid tracking, the non-rigid tracking recovers non-rigid motion parameters. Since this method does not assume any 3D projection information and priors of the guidewire shape, the guidewire shape and motion in a 2D plane is very flexible. To prevent the possible over-deformation of a guidewire, the matching score in the non-rigid tracking is a combination of a matching score between the template and current guidewire features, and smoothness constraints that are imposed on the guidewire shape. Accordingly, the matching score $E(\vec{u})$ of a non-rigid motion parameter $\vec{u}$ can be defined in Equation (3):

$$E(\vec{u}) = E_m(\vec{u}) + E_s(\vec{u}) \quad (3)$$
$$= \sum_i \sum_j \exp\left\{ -\frac{|T(i;\vec{u}) - I(j)|^2}{2\sigma^2} \right\} + \alpha \int \left| \frac{d\Gamma(\vec{u})}{ds} \right|^2 ds +$$
$$\beta \int \left| \frac{d^2 \Gamma(\vec{u})}{ds^2} \right|^2 ds.$$

In Equation (3), $E_m(\vec{u})$ is a matching score, which is defined in the same way as in the rigid tracking. The only difference is that the transformation $\vec{u}$ in Equation (3) is non-rigid and can be very flexible. $E_s(\vec{u})$ is a smoothness constrain term that consists of two parts from the first-order and second-order derivatives of the guidewire curve under the non-rigid deformation $\vec{u}$. $\alpha$ and $\beta$ are coefficients to balance the energy terms of matching error and of smoothness constraint.

Figure 5:
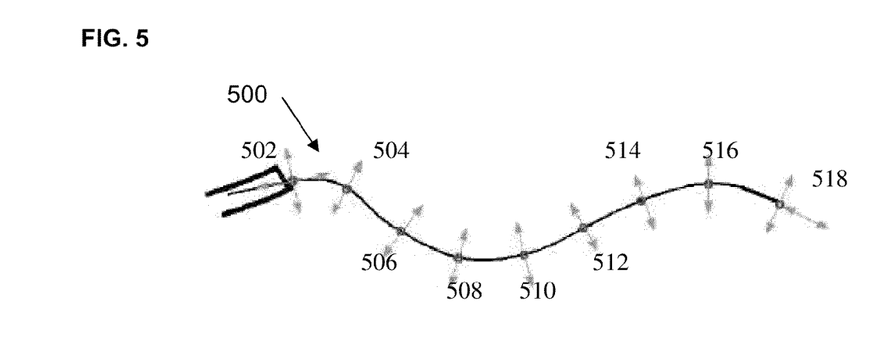
FIG. 5 illustrates exemplary non-rigid guidewire deformation.

To find the non-rigid guidewire motion $\vec{u}$, the non-rigid tracking method utilizes a scheme in which control points space along the guidewire are deformed to achieve a maximum matching score. FIG. 5 illustrates exemplary non-rigid guidewire deformation. As illustrated in FIG. 5, control points 520, 504, 506, 508, 510, 512, 514, and 518 on an exemplary guidewire spline 500 are deformed. Due to the flexibility of guidewire motion, the search space of the non-rigid motion parameter $\vec{u}$ is high dimensional. As illustrated in FIG. 5, to reduce the dimensionality of the searching space, control points 504-516 on the guidewire body are deformed along normal directions, and control points 502 and 518 at the end of the guidewire are deformed along both the tangent and normal directions. However, to exhaustively explore such a deformation space is still formidable considering computational complexity. For example, if there are 20 control points, and each control point has 10 deformation candidates, the searching space contains $10^{20}$ candidates. Instead of parallely searching the search space, according to an advantageous embodiment of the present invention, the method searches the guidewire deformation sequentially. At each step, only one control point deforms to achieve a maximum matching score. The sequential deformation will iterate until a maximum number of iterations is reached or it converges. Similar to the rigid tracking described above, a multi-resolution searching strategy is applied during the non-rigid tracking. The sequential searching strategy is first applied at a coarse resolution with a greater σ, and then applied at finer resolution with smaller σ. The sequential non-rigid tracking in most cases leads to a global optimal solution, because the rigid tracking has roughly aligned the guidewire near the true shape. After the non-rigid tracking, the tracking of the guidewire from the previous frame to the current frame is complete. Image (c) of FIG. 3 shows the final guidewire tacking result 304 resulting from the non-rigid deformation.

Returning to FIG. 2, at step 210, the guidewire tracking results for the fluoroscopic image sequence are output. For example, the guidewire tracking results can be output by displaying the fluoroscopic images in the sequence showing the tracked guidewire in each image. Such images show that the guidewire detection results can be used, for example, in image-guided coronary intervention.

Figure 6:
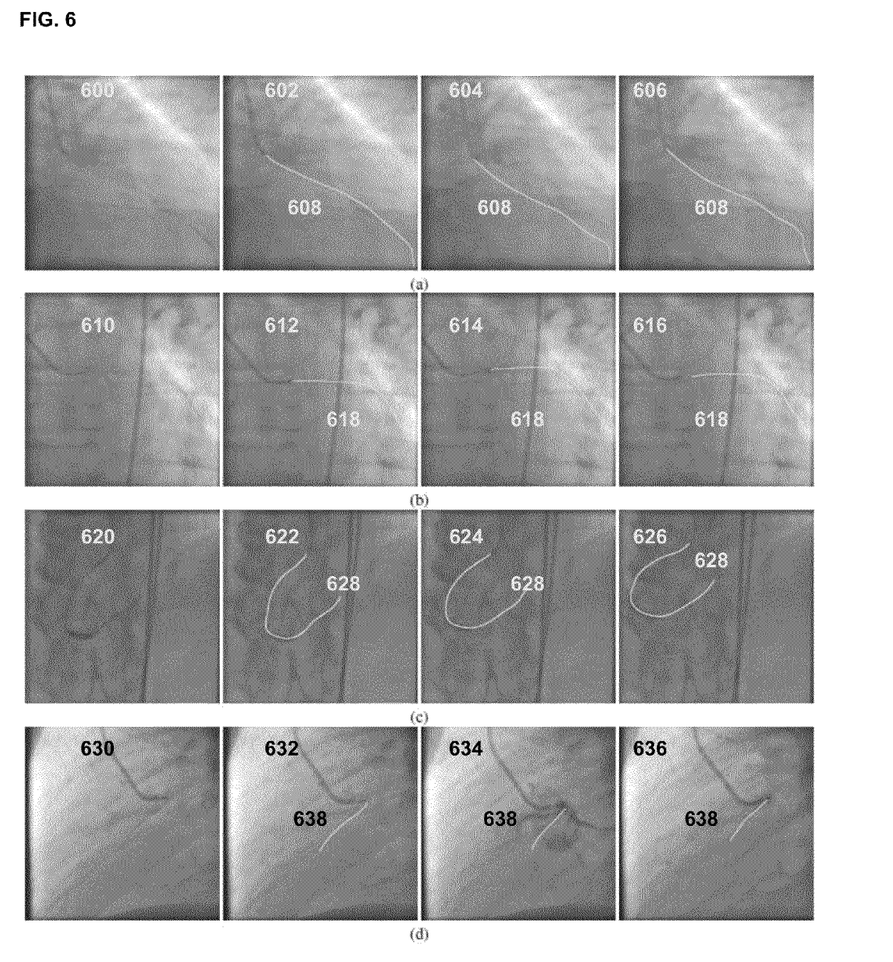
FIG. 6 illustrates exemplary guidewire tracking results generated using the method of FIG. 2.

FIG. 6 illustrates exemplary guidewire tracking results generated using the method of FIG. 2. In particular, FIG. 6 shows exemplary partial fluoroscopic image sequences (a), (b), (c), and (d) showing guidewires tracked using the method of FIG. 2. In sequence (a), image 600 is the first frame of the sequence and images 602, 604, and 606 are frames showing the tracked guidewire 608. In sequence (b), image 610 is the first frame of the sequence and images 612, 614, and 616 are frames showing the tracked guidewire 618. In sequence (c), image 620 is the first frame of the sequence and images 622, 624, and 626 are frames showing the tracked guidewire 628. In sequence (d), image 630 is the first frame of the sequence and images 632, 634, and 636 are frames showing the tracked guidewire 638.

Figure 7:
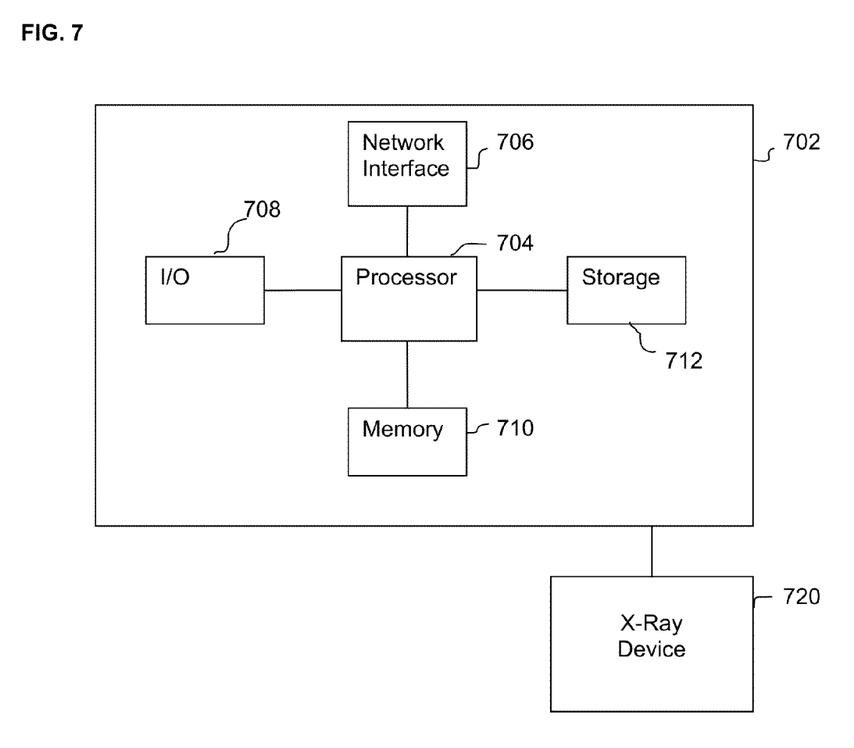
FIG. 7 is a high level block diagram of a computer capable of implementing the present invention.

The above-described methods for guidewire tracking in fluoroscopic image sequences may be implemented on a computer using well-known computer processors, memory units, storage devices, computer software, and other components. A high level block diagram of such a computer is illustrated in FIG. 7. Computer 702 contains a processor 704 which controls the overall operation of the computer 702 by executing computer program instructions which define such operation. The computer program instructions may be stored in a storage device 712, or other computer readable medium, (e.g., magnetic disk) and loaded into memory 710 when execution of the computer program instructions is desired. Thus, all method steps described above, including the method steps illustrated in FIG. 2, may be defined by the computer program instructions stored in the memory 710 and/or storage 712 and controlled by the processor 704 executing the computer program instructions. An image acquisition device 720, such as an X-ray imaging device, can be connected to the computer 702 to input fluoroscopic image sequences to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.) One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for tracking a guidewire in a fluoroscopic image sequence, comprising:
   detecting guidewire segments in a plurality of frames of the fluoroscopic image sequence;
   detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame; and
   non-rigidly deforming the detected guidewire in the current frame based on the rigidly tracked guidewire position and shape and the detected guidewire segments in the current frame.

2. The method of claim 1, wherein said step of detecting guidewire segments in a plurality of frames of the fluoroscopic image sequence comprises:
   detecting guidewire segments in each of the plurality of frames using a learning based guidewire segment detector.

3. The method of claim 2, wherein said learning based guidewire segment detector is trained using a probabilistic boosting tree (PBT).

4. The method of claim 1, wherein said step of detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame comprises:
   calculating a rigid transformation that tracks the guidewire from the previous frame to the current frame based on maximizing matching scores between a guidewire shape template corresponding to the guidewire position and shape from the previous frame under a rigid transformation and the detected guidewire segments in the current frame.

5. The method of claim 4, wherein said step of calculating a rigid transformation that tracks the guidewire from the previous frame to the current frame based on maximizing matching scores between a guidewire shape template corresponding to the guidewire position and shape from the previous frame under a rigid transformation and the detected guidewire segments in the current frame comprises:
   calculating the matching scores between the guidewire shape template under a rigid transformation and detected guidewire segments at the current frame; and
   rigidly tracking the guidewire from the previous frame to the current frame at a plurality of resolutions based on a variable kernel size in calculating the matching scores.

6. The method of claim 5, wherein said step of rigidly tracking the guidewire from the previous frame to the current frame at a plurality of resolutions based on a variable kernel size in calculating the matching scores comprises:
adaptively varying the kernel size in calculating the matching scores at a plurality of resolutions.

7. The method of claim 1, wherein said step of detecting a guidewire position in a current frame of the fluoroscopic image sequence by rigidly tracking the guidewire position and shape from a previous frame of the fluoroscopic image sequence based on a guidewire position and shape in the previous frame and the detected guidewire segments in the current frame comprises:
globally tracking the guidewire at a plurality of resolutions from the previous frame to the current frame; and
locally tracking a plurality of local segments of the guidewire at a plurality of resolutions from the previous frame to the current frame.

8. The method of claim 1, wherein said step of non-rigidly deforming the detected guidewire in the current frame based on the rigidly tracked guidewire position and shape and the detected guidewire segments in the current frame comprises:
deforming a plurality of control points on the detected guidewire in the current frame.

9. The method of claim 8, wherein said step of deforming a plurality of control points on the detected guidewire in the current frame comprises:
deforming control points on ends of the detected guidewire along tangent and normal directions to the detected guidewire; and
deforming remaining control points on the detected guidewire along normal directions to the detected guidewire.

10. The method of claim 8, wherein said step of deforming a plurality of control points on the detected guidewire in the current frame comprises:
sequentially deforming each of the plurality of control points to achieve a maximum matching score based on the rigidly detected guidewire position and shape and the detected guidewire segments in the current frame; and
iterating said step of sequentially deforming each of the plurality of control points to generate a final guidewire tracking result for the current frame.

11. The method of claim 8, wherein said step of deforming a plurality of control points on the detected guidewire in the current frame comprises:
deforming a plurality of control points on the detected guidewire in the current frame at a plurality of resolutions.

12. The method of claim 11, wherein said step of deforming a plurality of control points on the detected guidewire in the current frame comprises:
adaptively selecting a kernel size in calculating matching scores in deforming each control point at each of a plurality of resolutions.

13. The method of claim 1, further comprising:
repeating said step of detecting a guidewire position in a current frame of the fluoroscopic image sequence and said step of non-rigidly deforming the detected guidewire in the current frame for each of the plurality of frames of the fluoroscopic image sequence.

14. An apparatus for tracking a guidewire in a fluoroscopic image sequence, comprising:
means for detecting guidewire segments in a plurality of frames of the fluoroscopic image sequence;
means for detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame; and
means for non-rigidly deforming the detected guidewire in the current frame based on the rigidly tracked guidewire position and shape and the detected guidewire segments in the current frame.

15. The apparatus of claim 14, wherein said means for detecting guidewire segments in a plurality of frames of the fluoroscopic image sequence comprises:
detecting guidewire segments in each of the plurality of frames using a learning based guidewire segment detector.

16. The apparatus of claim 14, wherein said means for detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame:
means for calculating a rigid transformation that tracks the guidewire from the previous frame to the current frame based on maximizing matching scores between a guidewire shape template corresponding to the guidewire position and shape from the previous frame under a rigid transformation and the detected guidewire segments in the current frame.

17. The apparatus of claim 14, wherein said means for detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame comprises:
means for globally tracking the guidewire at a plurality of resolutions from the previous frame to the current frame; and
means for locally tracking a plurality of local segments of the guidewire at a plurality of resolutions from the previous frame to the current frame.

18. The apparatus of claim 14, wherein said means for non-rigidly deforming the detected guidewire in the current frame based on the rigidly tracked guidewire position and shape and the detected guidewire segments in the current frame:
means for deforming a plurality of control points on the detected guidewire in the current frame.

19. The apparatus of claim 18, wherein said means for deforming a plurality of control points on the detected guidewire in the current frame comprises:
means for deforming control points on ends of the detected guidewire along tangent and normal directions to the detected guidewire; and
means for deforming remaining control points on the detected guidewire along normal directions to the detected guidewire.

20. A non-transitory computer readable medium encoded with computer executable instructions for tracking a guidewire in a fluoroscopic image sequence, the computer executable instructions defining steps comprising:
detecting guidewire segments in a plurality of frames of the fluoroscopic image sequence;
detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame; and non-rigidly deforming the detected guidewire in the current frame based on the rigidly tracked guidewire position and shape and the detected guidewire segments in the current frame.

21. The non-transitory computer readable medium of claim 20, wherein the computer executable instructions defining the step of detecting guidewire segments in a plurality of frames of the fluoroscopic image sequence comprise computer executable instructions defining the step of:

detecting guidewire segments in each of the plurality of frames using a learning based guidewire segment detector.

22. The non-transitory computer readable medium of claim 20, wherein the computer executable instructions defining the step of detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame comprise computer executable instructions defining the step of:

calculating a rigid transformation that tracks the guidewire from the previous frame to the current frame based on maximizing matching scores between a guidewire shape template corresponding to the guidewire position and shape from the previous frame under a rigid transformation and the detected guidewire segments in the current frame.

23. The non-transitory computer readable medium of claim 22, wherein the computer executable instructions defining the step of calculating a rigid transformation that tracks the guidewire from the previous frame to the current frame based on maximizing matching scores between a guidewire shape template corresponding to the guidewire position and shape from the previous frame under a rigid transformation and the detected guidewire segments in the current frame comprise computer executable instructions defining the step of:

calculating the matching scores between the guidewire shape template under a rigid transformation and detected guidewire segments at the current frame; and rigidly tracking the guidewire from the previous frame to the current frame at a plurality of resolutions based on a variable kernel size in calculating the matching scores.

24. The non-transitory computer readable medium of claim 23, wherein the computer executable instructions defining the step of rigidly tracking the guidewire from the previous frame to the current frame at a plurality of resolutions based on a variable kernel size in calculating the matching scores comprise computer executable instructions defining the step of:

adaptively varying the kernel size in calculating the matching scores at a plurality of resolutions.

25. The non-transitory computer readable medium of claim 20, wherein the computer executable instructions defining the step of detecting a guidewire position in a current frame of the fluoroscopic image sequence by rigidly tracking a guidewire position and shape from a previous frame of the fluoroscopic image sequence based on the guidewire position and shape in the previous frame and the detected guidewire segments in the current frame comprise computer executable instructions defining the steps of:

globally tracking the guidewire at a plurality of resolutions from the previous frame to the current frame; and locally tracking a plurality of local segments of the guidewire at a plurality of resolutions from the previous frame to the current frame.

26. The non-transitory computer readable medium of claim 20, wherein the computer executable instructions defining the step of non-rigidly deforming the detected guidewire in the current frame based on the rigidly tracked guidewire position and shape and the detected guidewire segments in the current frame comprise computer executable instructions defining the step of:

deforming a plurality of control points on the detected guidewire in the current frame.

27. The non-transitory computer readable medium of claim 26, wherein the computer executable instructions defining the step of deforming a plurality of control points on the detected guidewire in the current frame comprise computer executable instructions defining the steps of:

deforming control points on ends of the detected guidewire along tangent and normal directions to the detected guidewire; and deforming remaining control points on the detected guidewire along normal directions to the detected guidewire.

28. The non-transitory computer readable medium of claim 26, wherein the computer executable instructions defining the step of deforming a plurality of control points on the detected guidewire in the current frame comprise computer executable instructions defining the steps of:

sequentially deforming each of the plurality of control points to achieve a maximum matching score based on the rigidly detected guidewire position and shape and the detected guidewire segments in the current frame; and iterating said step of sequentially deforming each of the plurality of control points to generate a final guidewire tracking result for the current frame.

29. The non-transitory computer readable medium of claim 26, wherein the computer executable instructions defining the step of deforming a plurality of control points on the detected guidewire in the current frame comprise computer executable instructions defining the step of:

deforming a plurality of control points on the detected guidewire in the current frame at a plurality of resolutions.

30. The non-transitory computer readable medium of claim 20, further comprising computer executable instructions defining the step of:

repeating said step of detecting a guidewire position in a current frame of the fluoroscopic image sequence and said step of non-rigidly deforming the detected guidewire in the current frame for each of the plurality of frames of the fluoroscopic image sequence.

* * * * *